(12) United States Patent
Al-Ali

(10) Patent No.: US 8,418,524 B2
(45) Date of Patent: Apr. 16, 2013

(54) NON-INVASIVE SENSOR CALIBRATION DEVICE

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 371 days.

(21) Appl. No.: 12/813,782

(22) Filed: Jun. 11, 2010

(65) Prior Publication Data

US 2011/0023575 A1 Feb. 3, 2011

Related U.S. Application Data

(60) Provisional application No. 61/186,765, filed on Jun. 12, 2009.

(51) Int. Cl.
*G01N 21/93* (2006.01)

(52) U.S. Cl.
USPC .............................. 73/1.56; 73/1.02; 600/331

(58) Field of Classification Search ................... 73/1.02, 73/1.56; 600/331
See application file for complete search history.

(56) References Cited

U.S. PATENT DOCUMENTS

| | | | |
|---|---|---|---|
| 4,834,532 A * | 5/1989 | Yount | 356/41 |
| 4,964,408 A | 10/1990 | Hink et al. | |
| 5,041,187 A | 8/1991 | Hink et al. | |
| 5,069,213 A | 12/1991 | Polczynski | |
| 5,278,627 A | 1/1994 | Aoyagi et al. | |
| 5,337,744 A | 8/1994 | Branigan | |
| 5,341,805 A | 8/1994 | Stavridi et al. | |
| 5,377,676 A | 1/1995 | Vari et al. | |
| 5,452,717 A | 9/1995 | Branigan et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |

(Continued)

*Primary Examiner* — David Rogers
(74) *Attorney, Agent, or Firm* — Knobbe Martens Olson & Bear, LLP

(57) ABSTRACT

A calibration device according to embodiments of the disclosure is capable of being used with a non-invasive sensor. Certain embodiments of the calibration device simulate a human pulse by varying the volume of blood being measured by the optical sensor. Further, embodiments of the calibration device allow the generation of calibration curves or data for measured parameters over larger ranges of measured values compared to patient-based calibration.

12 Claims, 7 Drawing Sheets

U.S. PATENT DOCUMENTS

| | | | |
|---|---|---|---|
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,321,100 | B1 | 11/2001 | Parker |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Pishney et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,062,975 | B2 * | 6/2006 | Schmid et al. ................ 73/756 |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |

| | | |
|---|---|---|
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |

* cited by examiner

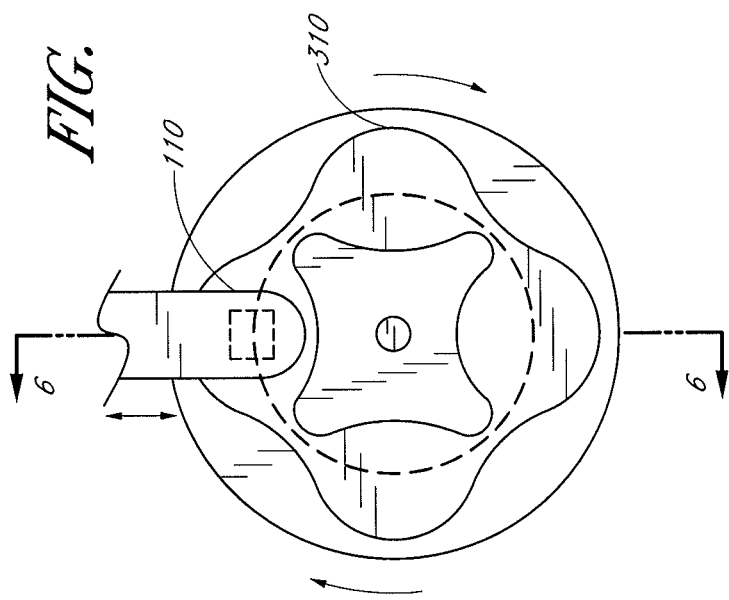
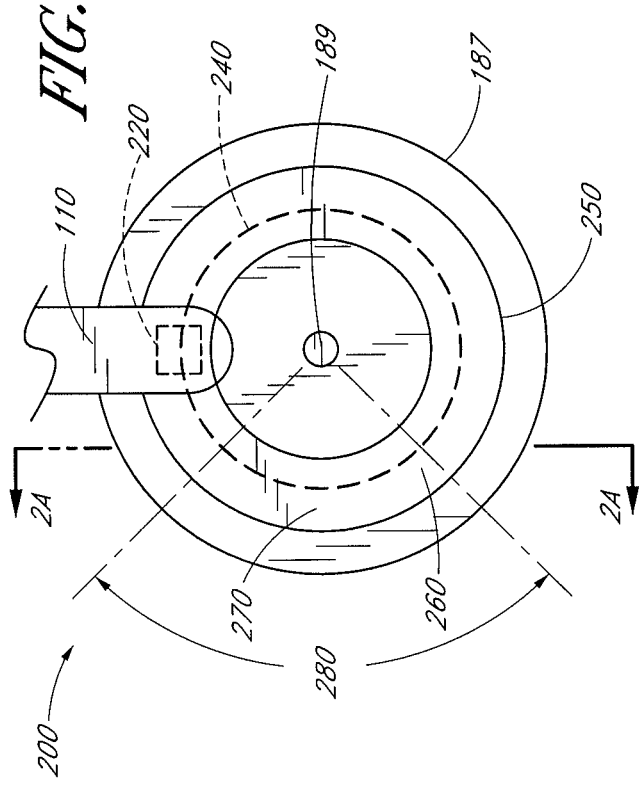
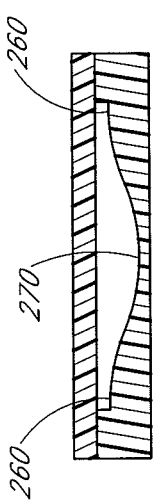

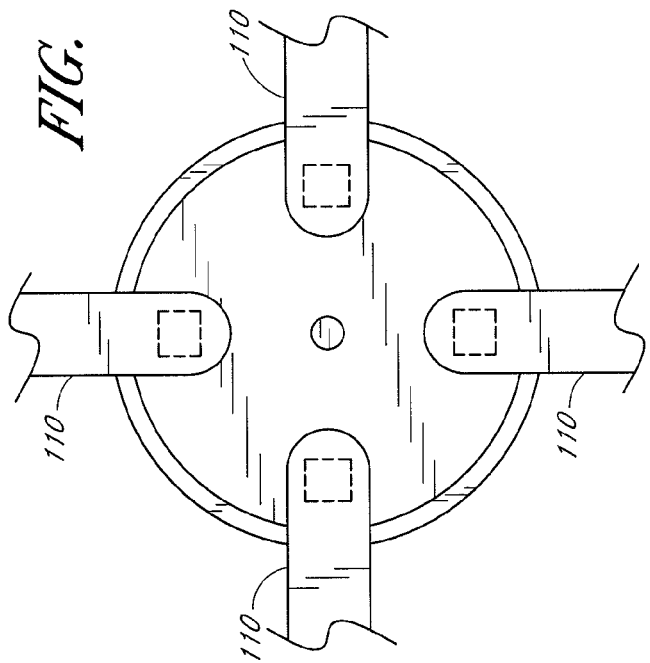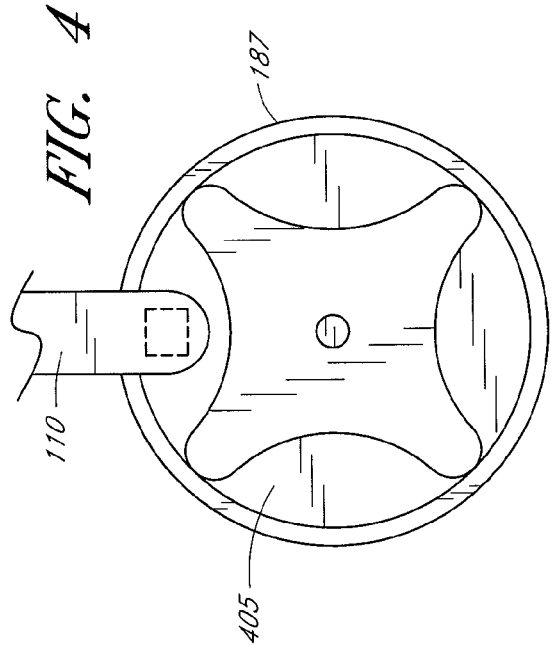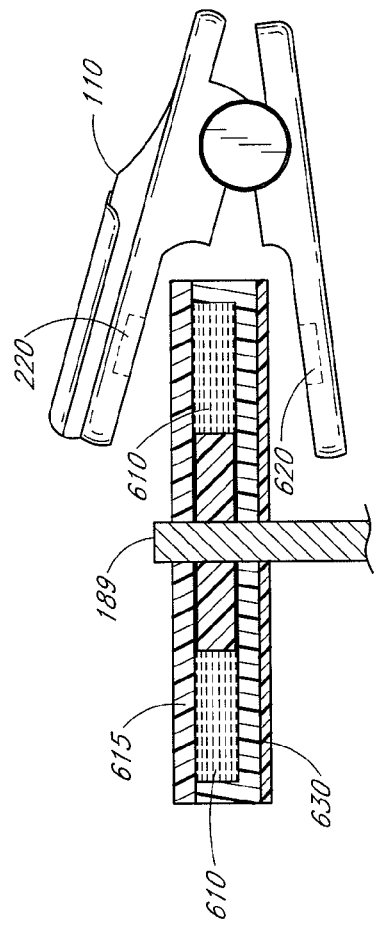

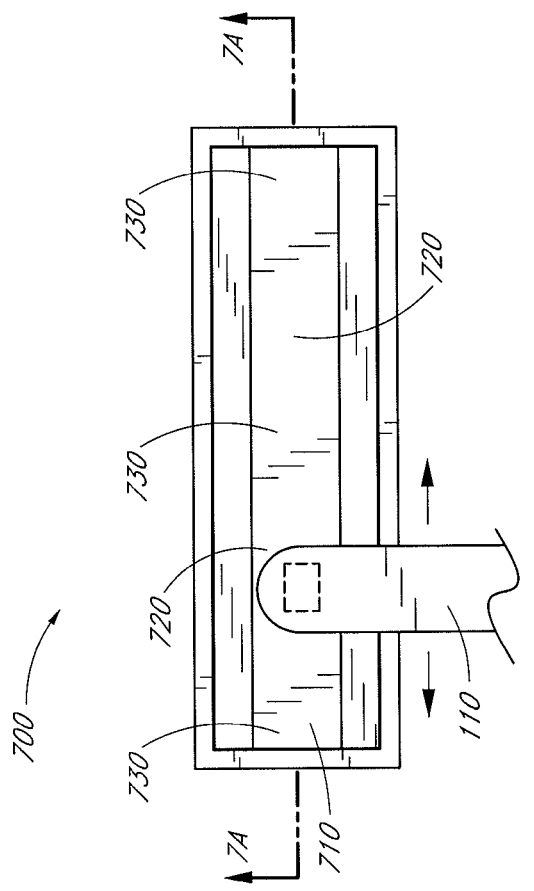
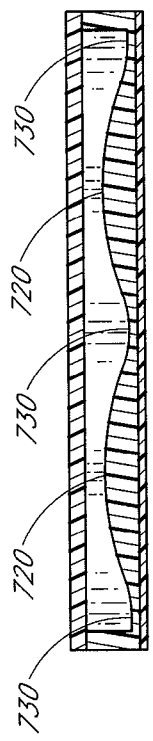
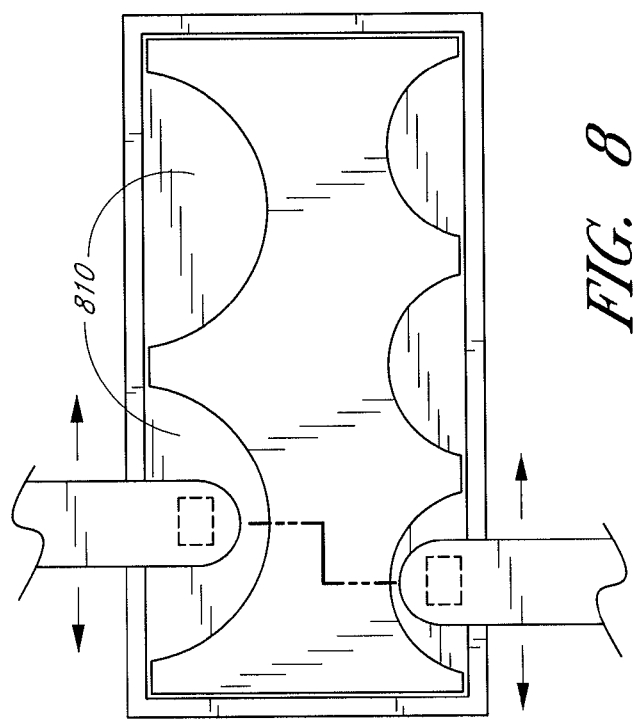
FIG. 7
FIG. 7A
FIG. 8

NON-INVASIVE SENSOR CALIBRATION DEVICE

CROSS-REFERENCE TO RELATED APPLICATIONS

The present application claims priority benefit under 35 U.S.C. §119 (e) from U.S. Provisional Application No. 61/186,765, filed Jun. 12, 2009, entitled "Non-invasive Optical Sensor Calibration Device," which is incorporated herein by reference in its entirety.

FIELD OF THE DISCLOSURE

The present disclosure relates to medical sensors and specifically to devices for calibration of noninvasive optical sensors.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methenoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity pulse oximeters capable of reading through motion induced noise are disclosed in U.S. Pat. Nos. 6,770, 028, 6,658,276, 6,157,850, 6,002,952 5,769,785, and 5,758, 644, which are assigned to Masimo Corporation ("Masimo") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations and/or glucose concentrations, as a few examples. Advanced physiological monitors and corresponding multiple wavelength optical sensors capable of measuring parameters in addition to SpO2, such as HbCO, HbMet and/or Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo.

The accuracy of patient monitors, generally, and oximeter systems, specifically, can be critical to the care and diagnosis of a patient being monitored. Therefore, proper calibration of patient monitors and noninvasive sensors is desirable.

SUMMARY OF THE INVENTION

As such it is desirable to provide a calibration device that can produce repeatable and/or reliable calibration data. Due to manufacturing tolerances, the wavelengths emitted by sensors, such as by the LEDs used in pulse oximeters, can vary from the specified wavelength of the sensor. The light absorption of hemoglobin is strongly dependant on the wavelength emitted by the LED. Thus, the accuracy of the monitor depends on the closeness of the sensor's wavelength to the specified wavelength of the sensor used to generate the stored values on the monitor. One method of calibrating sensors measures the exact wavelength of an LED and filters out LEDs that differ more than a predetermined limit from the specified wavelength. Another method of calibration uses colored films to generate a value using the sensor and filters out sensors that differ more than a predetermined limit from the expected value. However, these calibration methods can be costly, time consuming, and/or inaccurate.

It is therefore desirable to provide repeatable and/or reliable calibration data that can compensate for variations in the sensors. A calibration device, according to embodiments of the disclosure, can simulate a patient's pulse and/or provide repeatable and/or reliable measurements across time.

In order to increase reliability, another aspect of this disclosure uses blood samples or models of known measured parameters for calibration measurements. Further, blood samples or models demonstrating a wider range of measureable parameters can be used to generate calibration data for greater ranges than values ordinarily found in human blood.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit its scope. Throughout the drawings, reference numbers are reused to indicate correspondence between referenced elements.

FIG. 2 illustrates a simplified top view of a noninvasive sensor calibration device according to an embodiment of the disclosure;

FIG. 2A illustrates a cross-section of the calibration device of FIG. 2 taken along a channel;

FIG. 3 illustrates a simplified top view of an embodiment of the disclosure where the channel width varies from narrow to wider portions;

FIG. 4 illustrates a simplified top view of an embodiment of the disclosure wherein the disk includes separate chambers for holding blood;

FIG. 5 illustrates a simplified top view of an embodiment for calibrating multiple sensors;

FIG. 6 illustrates a cross-sectional view through the center of the calibration disk of FIG. 1;

FIG. 7 illustrates a simplified top-view of another embodiment of the disclosure wherein a rectangular container for the blood is used;

FIG. 7A illustrates a cross section of the container of FIG. 7 taken along a channel;

FIG. 8 illustrates one embodiment of the disclosure where a rectangular container has one or more chambers along its edge.

DETAILED DESCRIPTION OF THE PREFERRED EMBODIMENT

Figure 1A:
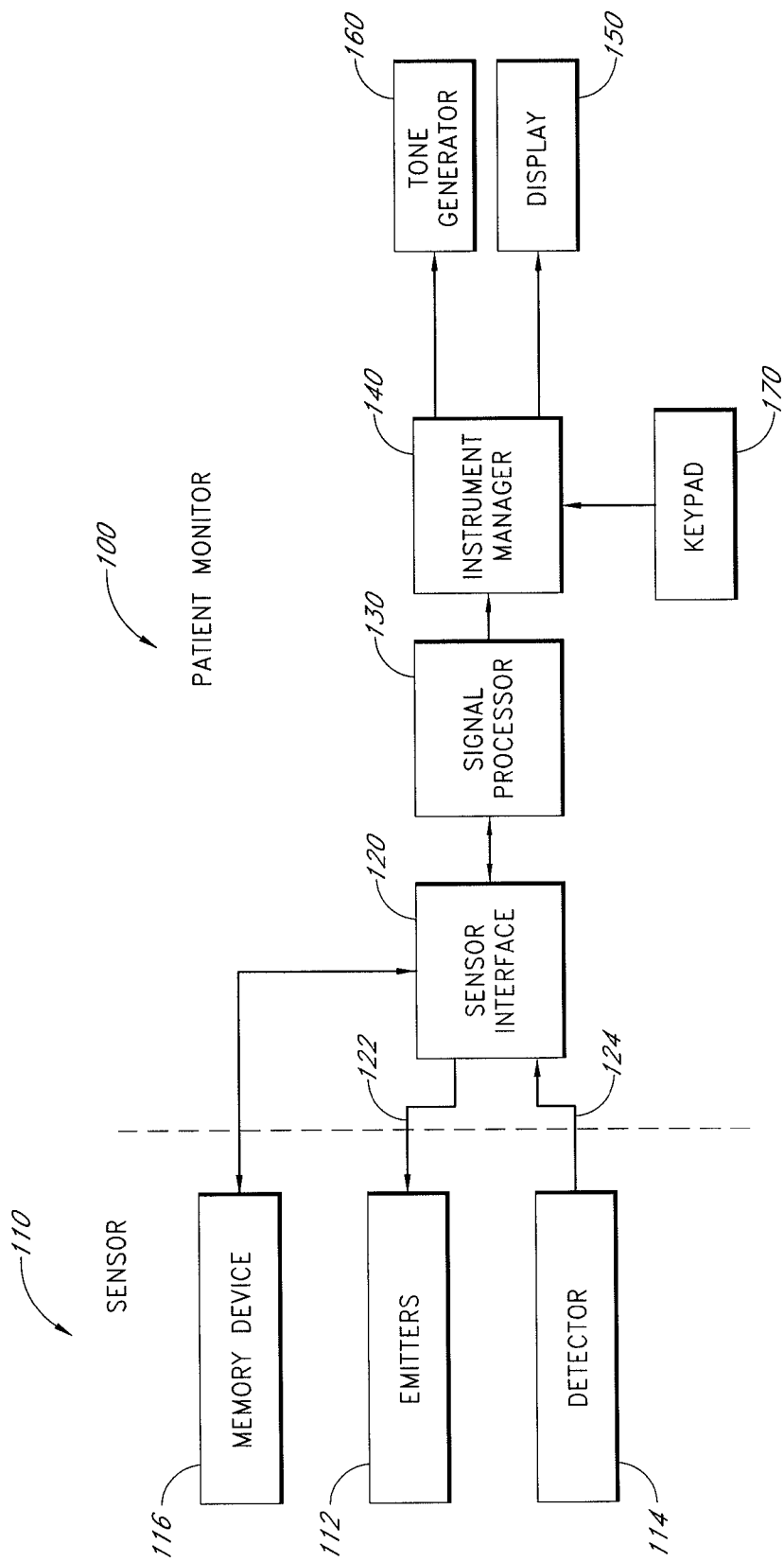
FIG. 1A illustrates a block diagram of a patient monitoring system, such as a pulse oximeter.

FIG. 1 illustrates a patient monitor 100, such as a pulse oximeter, and associated sensor 110. Generally, in the case of a pulse oximeter, the sensor 110 has LED emitters 112, generally one at a red wavelength and one at an infrared wavelength, and a photodiode detector 114. The sensor 110 is generally attached to an adult patient's finger, ear, forehead, or an infant patient's foot, though can be attached to other tissue sites. For a finger, the sensor 110 is configured so that the emitters 112 project light through the fingernail and through the blood vessels and capillaries underneath. The LED emitters 112 are activated by drive signals 122 from the pulse oximeter 100. The detector 114 is positioned at the fingertip opposite the fingernail so as to detect the LED emitted light as it emerges from the finger tissues. The photodiode generated signal 124 is relayed by a cable to the pulse oximeter 100.

A pulse oximeter 100 determines oxygen saturation ($SpO_2$) by computing the differential absorption by arterial blood of the two wavelengths emitted by the sensor 110. A typical pulse oximeter 100 contains a sensor interface 120, a $SpO_2$ processor 130, an instrument manager 140, a display 150, an audible indicator (tone generator) 160, and a keypad 170. The sensor interface 120 provides LED drive current 122 which alternately activates the sensor's red and infrared LED emitters 112. The sensor interface 120 also has input circuitry for amplification and filtering of the signal 124 generated by the photodiode detector 114, which corresponds to the red and infrared light energy attenuated from transmission through the patient tissue site. The $SpO_2$ processor 130 calculates a ratio of detected red and infrared intensities, and an arterial oxygen saturation value is empirically determined based on that ratio. The instrument manager 140 provides hardware and software interfaces for managing the display 150, audible indicator 160, and keypad 170. The display 150 shows the computed oxygen saturation status, as described above. Similarly, other patient parameters including HbCO, HbMet, Hbt, Hct, oxygen concentrations, glucose concentrations, pulse rate, PI, SiQ, and/or PVI can be computed. The audible indicator 160 provides the pulse beep as well as alarms indicating desaturation events. The keypad 170 provides a user interface for such things as alarm thresholds, alarm enablement, and/or display options.

Computation of $SpO_2$ relies on the differential light absorption of oxygenated hemoglobin, $HbO_2$, and deoxygenated hemoglobin, Hb, to determine their respective concentrations in the arterial blood. Specifically, pulse oximetry measurements are made at red (R) and infrared (IR) wavelengths chosen such that deoxygenated hemoglobin absorbs more red light than oxygenated hemoglobin, and, conversely, oxygenated hemoglobin absorbs more infrared light than deoxygenated hemoglobin, for example 660 nm (R) and 905 nm (IR).

To distinguish between tissue absorption at the two wavelengths, the red and infrared emitters 112 are provided drive current 122 so that only one is emitting light at a given time. For example, the emitters 112 can be cycled on and off alternately, in sequence, with each only active for a quarter cycle and with a quarter cycle separating the active times. This allows for separation of red and infrared signals and removal of ambient light levels by downstream signal processing. Because only a single detector 114 is used, it responds to both the red and infrared emitted light and generates a time-division-multiplexed ("modulated") output signal 124. This modulated signal 124 is coupled to the input of the sensor interface 120.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, and/or the like, each of which absorbs light. It is assumed that the background absorption due to these surrounding tissues is invariant and can be ignored. Thus, blood oxygen saturation measurements are based upon a ratio of the time-varying or AC portion of the detected red and infrared signals with respect to the time-invariant or DC portion: $R/IR=(Red_{AC}/Red_{DC})/(IR_{AC}/IR_{DC})$.

The desired $SpO_2$ measurement is then computed from this ratio. The relationship between R/IR and $SpO_2$ can be determined by statistical regression of experimental measurements obtained from human volunteers and calibrated measurements of oxygen saturation. In a pulse oximeter device, this empirical relationship can be stored as a "calibration curve" in a read-only memory (ROM) look-up table so that $SpO_2$ can be directly read-out of the memory in response to input R/IR measurements. However, calibration measurements taken from human patients can be subject to variations as measured parameters change over time. Measurements taken may not be repeatable. Embodiments of the disclosure are directed towards a calibration device that simulates a human pulse and allows generation of calibration curves using the simulated pulse.

In an embodiment, the sensor 110 also includes a memory device 116. The memory can include any one or more of a wide variety of memory devices known to an artisan from the disclosure herein, including an EPROM, an EEPROM, a flash memory, a combination of the same or the like. The memory can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the memory can include the ROM, the RAM, single wire memories, combinations, or the like.

The memory device can advantageously store some or all of a wide variety data and information, including, for example, information on the type or operation of the sensor, type of patient or body tissue, buyer or manufacturer information, sensor characteristics including the number of wavelengths capable of being emitted, emitter specifications, emitter drive requirements, demodulation data, calculation mode data, software such as scripts, executable code, or the like, sensor electronic elements, sensor life data indicating whether some or all sensor components have expired and should be replaced, encryption information, monitor or algorithm upgrade instructions or data, or the like. In an embodiment, the memory device can also include emitter wavelength correction data and/or calibration factor including, for example, calibration information obtained using the calibration device of the present disclosure.

Figure 1B:
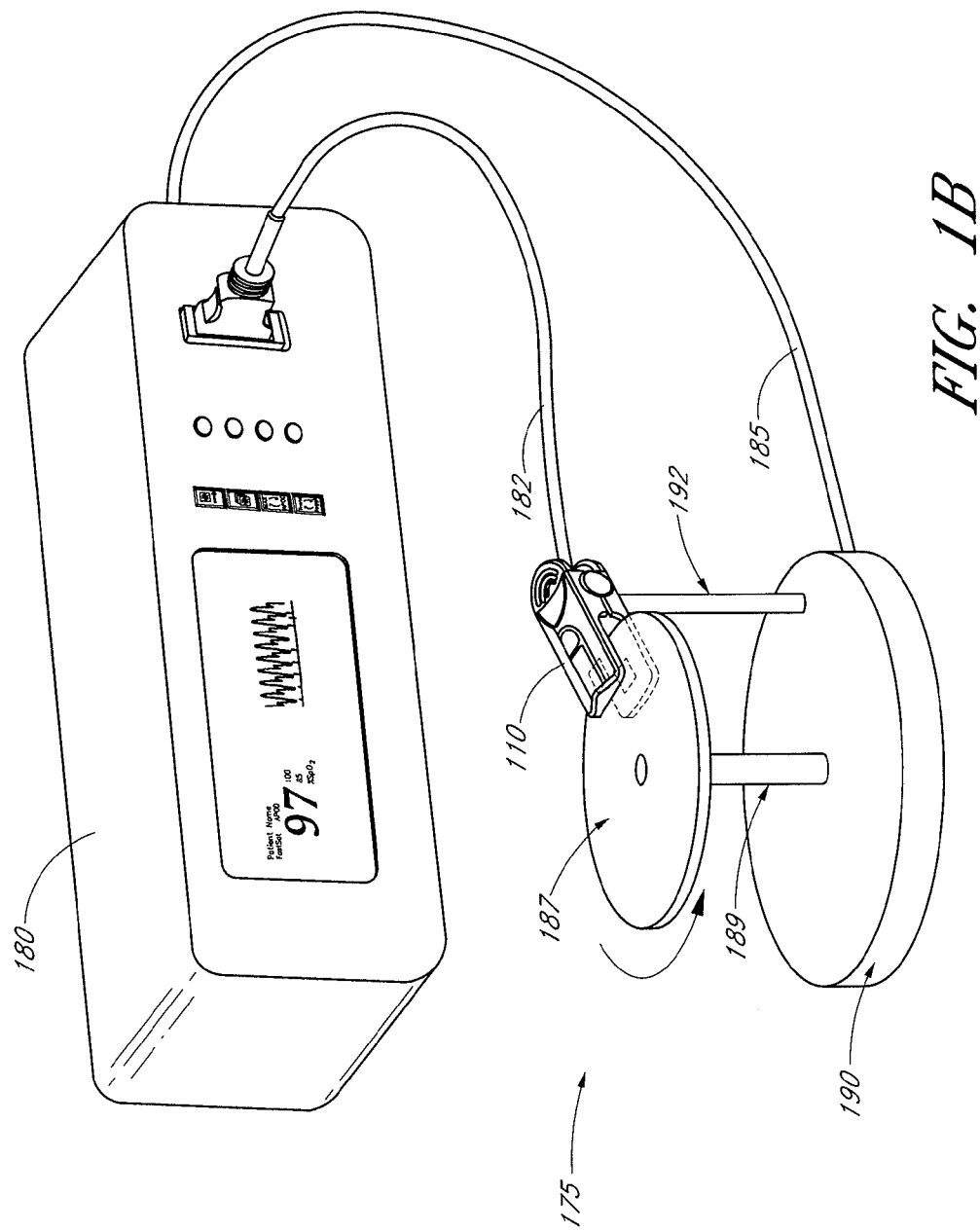
FIG. 1B illustrates an embodiment of a calibration system.

FIG. 1B illustrates an embodiment of a calibration system. The calibration system can include a calibration device 175, a sensor 110, and/or a calibration manager 180. The sensor 110 can be in communication via a communication medium 182 with the calibration manager 180 which analyzes the sensor output and determines calibration information for the sensor. The communication medium can be wired or wireless. In an embodiment, the calibration information can be stored directly on the sensor memory device. In an embodiment, the calibration manager is a patient monitor.

In the illustrated embodiment of FIG. 1B, the calibration device 175 can be connected to the calibration manager via a communication medium 185, such as a cable. The calibration manager can communicate with the calibration device 175 and control the operation of the calibration device. For example, the calibration manager 180 can speed up or slow down the calibration device to simulate changes in the pulse rate. The calibration manager 180 can also start and/or stop the calibration device and can do so to simulate a loss of signal. In some embodiments, the calibration device 175 can be independent of the calibration manager 180 and operates without additional input from the calibration manager 180.

The calibration device 175 can include a calibration plate or container 187 movably attached via a connector 189 to a base 190. A sensor holder 192 can be attached to the base 190. The base 190 can house electrical components, wires, logic circuits, and/or a motor.

FIG. 2 illustrates a simplified top view of a noninvasive sensor calibration device 200 according to an embodiment of the disclosure. The calibration device includes a container 187, in this embodiment, a disk configured to rotate about its center. In one embodiment, a noninvasive optical sensor, such as, for example, a pulse oximeter sensor 110, is placed around an edge of the disk. Emitters 220 can be placed above the disk 187, while a detector is placed below the disk. The detector can be aligned with the emitters to take measurements of a portion of the disk currently passing between the detector and the emitter. The position of the emitters 220 and the detector can be switched, with the emitter below the disk and the detector above the disk. The sensor can be connected to a calibration manager via a cable or other communication medium. For example, the detector outputs a signal to the manager over the cable which then processes the signal to provide a readout of physiological parameters such as oxygen saturation (SpO2) and/or pulse rate.

In some embodiments, the center of the disk 187 is attached to a connector, such as a spindle 189. The spindle 189 is attached to a motor that drives the rotation of the disk. In an embodiment, the disk rotates at a speed that simulates a blood flow of a patient. The disk can rotate faster to simulate a faster heart rate (HR) or slower for slower HR. In an embodiment, the disk rotates at about 1 Hz. As will be appreciated by skilled artisans, the disk can be rotated faster or slower to simulate a desired property.

As the disk rotates, the sensor 110 traverses along a track 240 of the disk. In the illustrated embodiment, a single channel lies along the rotational track 240 followed by the detector. The channel 250 is a recess formed on the disk that can contain a blood sample or model, such as blood or a blood substitute. The terms "sample" and "model" are used interchangeably in this application. The blood sample or model can be a solid, semi-solid, liquid or semi-liquid. The depth of the channel varies from a shallow portion 260 to a deep portion 270 holding a larger amount of blood. The change in depth creates a change in the volume of blood passing by the detector, the change in the volume of blood simulating a patient's pulse. The depth of the channel progressively increases from the shallow 260 portion to the deep portion 270 and then decreases to another shallow portion 260, defining one section 280 of the channel. In the illustrated embodiment, the disk includes four sections, though the number of sections can range from between one to four, or to more than four sections, depending on the speed of the rotation, the desired heart rate, the size of the container, and/or the like.

As the disk rotates, the sensor 110 measures one or more parameters of the passing blood. The measurements are communicated to the calibration manager 180, which determines a calibration factor for the sensor 110 based on the difference between the value of the measured parameter and the expected value of the parameter. For example, for a pulse oximeter sensor, the difference between measured and expected values can be caused by a difference between the wavelengths of the emitted light of the LEDs and the specific wavelengths of the LED used to generate the calibration curve. By using a calibration factor, a monitor can compensate for variations between sensors. The sensor 110 records the calibration factor in the memory device of the sensor. When the sensor 110 is next used, the sensor 110 can retrieve the stored calibration factor and communicate the calibration factor to its corresponding monitor. The monitor can then use the calibration factor to offset the measurements taken by the sensor and increase the accuracy of the measurements.

FIG. 2A illustrates a cross-section of a calibration device 200 of FIG. 2 taken along a channel. The volume of blood is least at the one or more shallow portions 260, 260 and greatest at the one or more deep portions 270. The volume of blood gradually increases from the shallow portion 260 to the deep portion 270. In one embodiment, the channel can have multiple shallow portions 260 and multiple deep portions 270, for example, the channel can be sinusoidal shaped.

As will be appreciated by skilled artisans, the pulse can be simulated in a variety of ways. For example, the volume of the blood being measured can be varied by changing the shape of the container. The volume can be varied by changing the width of the section as illustrated in FIG. 3. The volume can also be changed by varying the depth of the section while the width of the channel remains constant, as illustrated in FIG. 2 and FIG. 2A. In some embodiments, both the width and depth of the channel can be changed together to increase the range in the volume of blood. Furthermore, different ranges for depth of the blood can be used depending on the desired volume of blood. In certain embodiments, the depth of the blood varies from about 1 mm to about 3 mm. In some embodiments, the depth can be less than 1 mm. In certain embodiments, the depth can be greater than 3 mm. Likewise, different ranges for the width of the channel can be used depending on the desired volume of blood.

Additionally, the blood or blood substitute can be treated to contain the same, greater or lesser concentrations of a measured parameter, such as, for example, oxygenated hemoglobin, carboxyhemoglobin, methemoglobin, total hemoglobin, and/or fractional saturation, than normally found in a human. Calibration curves can be generated that cover a larger range of values than calibration curves generated only from measurements of humans. Likewise, sensors can be calibrated over a greater range. For certain embodiments, human blood can be used instead of blood substitutes. The use of human blood can provide better calibration data by more closely simulating the actual conditions under which the sensors will be used. Further, the use of human blood can allow calibration of sensors and/or monitors using blood from patients with different physiological conditions. Numerous patient characteristics can affect the accuracy of patient monitoring. The age, height and weight, race, and/or health status of a patient being monitored can affect readings detected by a sensor of a patient monitor. Compensating for these affects allows even greater accuracy than is accomplished by typical patient monitors. For example, the type of hemoglobin found in a patient can affect the absorption of energy attenuated through a patient monitoring site; as a specific example, the hemoglobin of a patient with sickle-cell anemia will absorb sensor light energy differently than a patient without that condition. By using human blood, calibration curves accounting for these various physiological differences can be generated.

As will be appreciated by skilled artisans from the disclosure provided herein, many different types of sensors can be used with the calibration device. In some embodiments, clip-style sensors can be calibrated using the device. The sensors are secured to a holder mechanism that holds the clip open over an edge of the calibration device. In certain embodiments, other types of sensors, such as, for example, multi-site, adhesive, and/or reusable sensors can be used. In some embodiments, an optical coherence tomography (OCT) sensor can be calibrated by the calibration system.

In certain embodiments, the container can further include a cover to prevent blood sample from spilling from the container. The cover can also prevent contamination of the blood sample. In certain embodiments, the container can be in two parts, with a top portion and a bottom portion. The top portion forms a cover and can be detached from the bottom portion. Once the top portion is detached, blood sample can be placed into the bottom portion. After filling the bottom portion, the container can be resealed. In some embodiments, the container is a single piece with one or more entry points for blood sample to be inserted into the container. In an embodiment, the entry point is a valve that allows blood into the container while allowing air to escape out. The blood can displace the air and fill the void vacated by the air. In an embodiment, the valve accepts syringes and/or needleless connectors, allowing for faster insertion of blood. The entry point can also be used as a drain to remove the blood sample from the container once the calibration process is completed. The container can further include a DC offset forming a layer under the container. The DC offset simulates the invariant portion or DC portion of human tissue, such as skin, muscle tissue and/or bone.

FIG. 3 illustrates a simplified top view of an embodiment of the disclosure where the channel 310 has a width that varies from a narrow to a wider portion. The change in width creates a change in the volume of blood sample passing by the sensor 110, the change in the volume of blood sample simulating a patient's pulse.

Referring to FIG. 2 and FIG. 3, the sections are interconnected with each other, allowing blood sample in different sections to mix together. The rotation of the disk can allow blood sample to flow within the channel, encouraging blood mixing. The blood sample mixing can reduce variations within different sections, allowing a more uniform measurement of parameters.

FIG. 4 illustrates another embodiment of the disclosure wherein the disks comprises of separate chambers for holding blood sample. A chamber 405 is a recess formed on the container or disk 187, separate from other chambers. In the illustrated embodiment, there are four chambers on the disk. A non-invasive sensor 110 is positioned over an edge of the disk. The volume of blood sample varies within the chamber. The volume of blood sample can be varied by changing the width of the chamber 405 from a narrow section to a wider section and/or by changing the depth of the chamber from a shallow section to a deep section. As the disk rotates, the sensor 110 traverses the chamber and measures varying volumes of blood sample. Some portions of the disk that pass by the sensor 110 can contain no blood sample. As will be appreciated by skilled artisans from the disclosure provided herein, the number of chambers 405 on the disk can be varied by changing the size of the chambers and/or by increasing the disk size. In some embodiments, one to four chambers are formed on the disk. In certain embodiments, more than four chambers are on the disk.

Separate chambers allow blood samples to remain separate from each other. Sensors and/or monitors can be calibrated using blood samples with different measurable parameter values on the same calibration device. Calibration measurements can be taken over a range of measurable values on the same calibration run.

FIG. 5 illustrates a simplified top view of an embodiment for calibrating multiple sensors. In FIG. 5, four sensors 110 are placed over the container or disk 187, allowing multiple sensors to be calibrated at the same time. In some embodiments, one to four sensors can be used. In other embodiments, more than four sensors can be used, depending on the size of the disk 187. Disks of larger diameter can allow more sensors to be calibrated at the same time. Furthermore, using multiple sensors can increase accuracy of the readings. One of the sensors can be already calibrated and provide a baseline reading for the other sensors. In some embodiments, each sensor can be connected to a separate calibration manager. Each calibration manager can generate calibration curves during the same calibration run.

FIG. 6 illustrates a cross-sectional view through the center of the calibration disk of FIG. 1. Blood is contained within the channel 610. The disk can further comprise a cover 615. The sensor 110 is placed over the edge of the disk to cover the blood sample contained in the disk. The sensor remains generally stable while the disk rotates. In one embodiment, the emitters 220 and the detector 620 are on opposite sides of the disk, aligned with each other. The disk can further comprise a DC offset 630 forming a layer under the disk. The disk can rotate around the spindle 189.

Figure 6B:
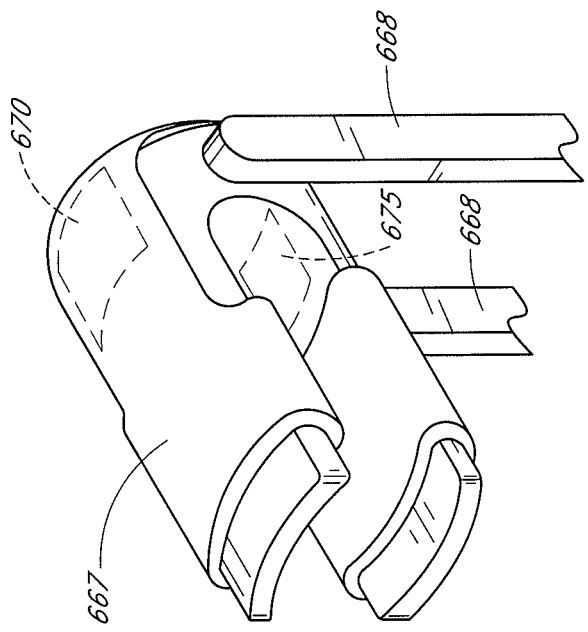
FIGS. 6A-B illustrate perspective views of an embodiment of a clip sensor holder.
Figure 6A:
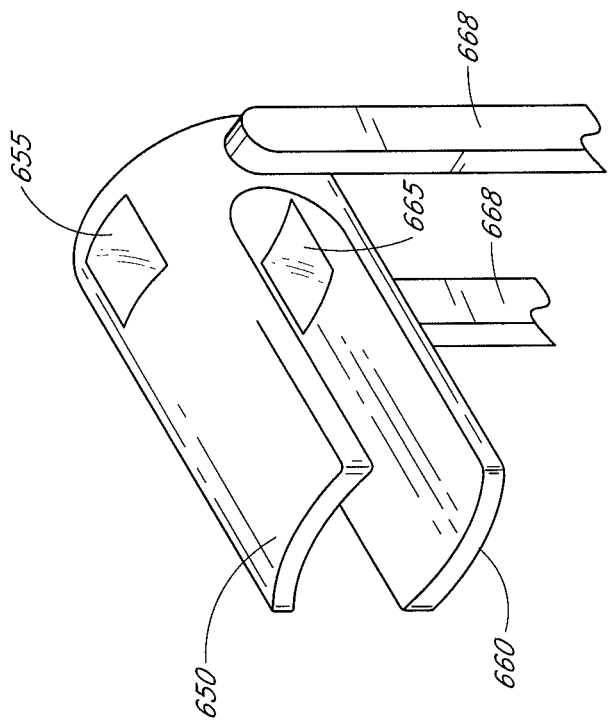

FIG. 6A and FIG. 6B illustrate perspective views of an embodiment of a sensor holder. Referring to FIG. 6A, an upper portion 650 includes an upper aperture 655 and the lower portion 660 includes a lower aperture 665. The apertures 655, 665 can be openings or clear material. The apertures 655, 665 generally allow for proper sensor operation. For example, the apertures 655, 665 allow for light from one or more emitters of the sensor to contact the blood sample in calibration device and for light attenuated by the blood sample in calibration device site to be received by a detector of the sensor. Referring to FIG. 6B, a sensor 667, such as an adhesive sensor, is held by the upper portion 650 and lower portion 660 of the sensor holder. One or more connectors 668 can connect the sensor holder to the base 190. In the illustrated embodiment, the sensor's detector 670 aligns with the upper aperture 655 and the sensor's emitters 675 aligns with the lower aperture. The positions of the detector 670 and emitters 675 can be reversed.

FIG. 7 illustrates a top-view of another embodiment of the disclosure wherein a rectangular container 700 for the blood sample is used. The container 700 comprises a channel 710 disposed on the surface of the container. The channel 710 can hold blood or a blood substitute. In the illustrated embodiment, the channel 710 comprises both shallow 720 and deep 730 portions. FIG. 7A illustrates a cross section of the container 700 of FIG. 7 taken along the channel 710. The volume of blood increases in the deep sections 730 and decreases in the shallow sections 720. One or more sensors 110 are placed over the edge to measure the parameters of the blood within the channel. The container 700 is attached to a driver that moves the container linearly back and forth past the sensor. In one embodiment, the width of the channel changes along the container, providing different volumes of blood sample for measurement to the sensor 110.

FIG. 8 illustrates one embodiment of the disclosure where a rectangular container has one or more chambers 810 along its edge. In some embodiments, chambers of different sizes can be used to simulate pulse variations, such as heart rate. In other embodiments, some or all of the chambers can be equal in size.

Figure 9:
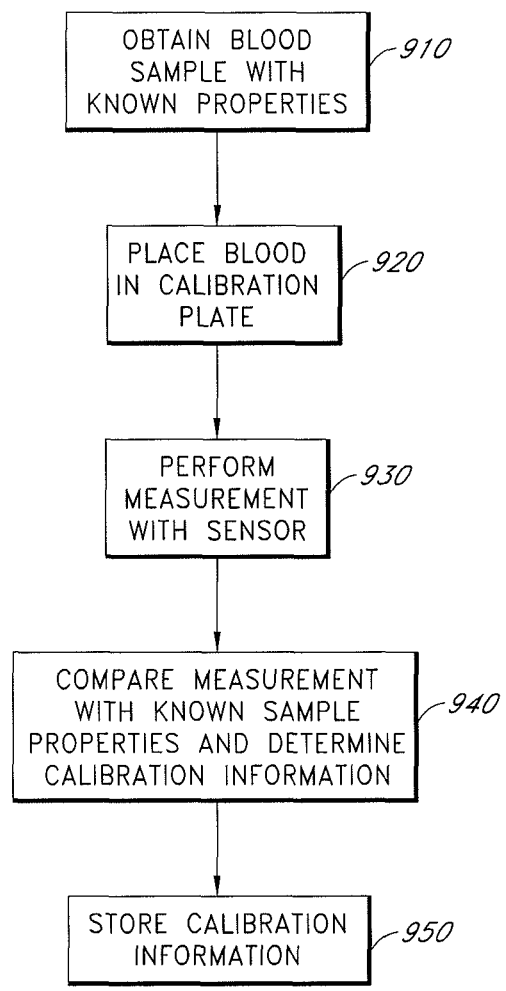
FIG. 9 illustrates a flow chart of an embodiment of the calibration process.

FIG. 9 illustrates a flow chart of an embodiment of the calibration process. At block 910, a blood sample with known properties is obtained. The known properties can be one or more measurable parameters that can include oxygen saturation, HbCO, HbMet, Hbt, Hct, oxygen concentrations, glucose concentrations, pulse rate, PI, SiQ, and/or PVI. The blood sample or model can be blood or a blood substitute.

At block 920, the blood sample is placed in a calibration plate or container 187, 700. One or more sensors 110 are positioned around the calibration plate. The one or more sensors can be connected to a calibration manager 180.

At block 930, the calibration system operates to perform measurements with the sensor 110. The measurements are communicated to the calibration manager via a communications medium 182. The measurements can be recorded by the calibration manager.

At block 940, the calibration manager 180 compares the measurements with the known sample properties and determines calibration information. For example, if the measured parameter is at variance with the known property, an offset can be calculated that compensates for the variance. In some embodiments, the values for the known property can be entered into the calibration manager before starting the calibration process. In certain embodiments, the calibration process can be run with an already calibrated sensor 110 in order to record baseline values for the blood sample in the calibration manager 180.

At block 950, the calibration information is stored. In some embodiments, the calibration information is stored on the sensor. For example, the calibration information can comprise of a calibration factor. The calibration factor can be stored on a memory device of the sensor and used to compensate for variances in the sensor readings. In certain embodiments, the calibration information is stored on the calibration manager 180. The calibration information can be used to generate calibration curves for patient monitors.

Various calibration devices have been disclosed in detail in connection with various embodiments. These embodiments are disclosed by way of examples only and are not to limit the scope of the claims that follow. One of ordinary skill in the art will appreciate the many variations, modifications and combinations. For example, the various embodiments of the calibration devices can be used with sensors and monitors that can measure any type of physiological parameter. In various embodiments, the sensor assemblies calibrated can be for any type of medical device. Further, embodiments of the calibration device can be used with sensors of various shapes, sizes, and attachment types.

Depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A calibration device for calibrating a noninvasive sensor, the calibration device comprising:
    a blood model container comprising at least one recess disposed on its surface, the at least one recess configured to move past a non-invasive sensor in order to generate at least one parameter measurement;
    a first portion of the at least one recess holding a first amount of blood model; and
    a second portion of the at least one recess holding a second amount of the blood model, wherein the second amount of the blood model in the second portion is greater than the first amount of the blood model held in the first portion.

2. The calibration device of claim 1, wherein the non-invasive sensor comprises a light emitting section and a light receiving section positioned around an edge of the blood model container, the light emitting section positioned over a side of the blood model container, the light receiving section positioned opposite the light emitting section over an opposite side of the blood model container, the blood model container movable through the light emitting section and the light-receiving section.

3. The calibration device of claim 2, wherein the first and second portions of the recess traverse the light emitting section and light receiving section of the sensor.

4. The calibration device of claim 1, wherein the blood model is at least partially liquid.

5. The calibration device of claim 1, wherein the container is a disk.

6. The calibration device of claim 5, further comprising:
    a driver for driving the blood model container past the sensor; and
    a spindle, the spindle connected to the center of the disk and to the driver, the driver rotating the spindle and the disk.

7. The calibration device of claim 1, wherein the blood model container is a rectangular container.

8. The calibration device of claim 7, further comprising a driver for driving the rectangular container linearly forward and backwards past the sensor.

9. The calibration device of claim 1, wherein the first portion is a different depth than the second portion.

10. The calibration device of claim 1, wherein the first portion is a different width than the second portion.

11. The calibration device of claim 1, wherein the blood container comprises two or more recesses.

12. The calibration device of claim 11 wherein the blood container comprises a first recess and a second recess, the first recess of a different size than the second recess.

* * * * *